(12) United States Patent
Gadakh et al.

(10) Patent No.: US 9,233,943 B2
(45) Date of Patent: Jan. 12, 2016

(54) PROCESS FOR SYNTHESIS OF SYN AZIDO EPDXIDE AND ITS USE AS INTERMEDIATE FOR THE SYNTHESIS OF AMPRENAVIR AND SAQUINAVIR

(71) Applicant: Council of Scientific & Industrial Research, New Delhi (IN)

(72) Inventors: Sunita Khanderao Gadakh, Maharashtra (IN); Reddy Santhosh Rekula, Maharashtra (IN); Arumugam Sudalai, Maharashtra (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/371,466

(22) PCT Filed: Jan. 10, 2013

(86) PCT No.: PCT/IN2013/000021
§ 371 (c)(1),
(2) Date: Jul. 10, 2014

(87) PCT Pub. No.: WO2013/105118
PCT Pub. Date: Jul. 18, 2013

(65) Prior Publication Data
US 2015/0011782 A1 Jan. 8, 2015

(30) Foreign Application Priority Data
Jan. 10, 2012 (IN) .............................. 82/DEL/2012

(51) Int. Cl.
| | |
|---|---|
| *C07C 247/04* | (2006.01) |
| *C07D 307/20* | (2006.01) |
| *C07D 301/14* | (2006.01) |
| *C07D 401/14* | (2006.01) |
| *C07D 401/12* | (2006.01) |
| *C07D 493/04* | (2006.01) |
| *C07D 301/02* | (2006.01) |

(52) U.S. Cl.
CPC ............ *C07D 301/14* (2013.01); *C07C 247/04* (2013.01); *C07D 301/02* (2013.01); *C07D 307/20* (2013.01); *C07D 401/12* (2013.01); *C07D 401/14* (2013.01); *C07D 493/04* (2013.01)

(58) Field of Classification Search
CPC .. C07D 301/14; C07D 307/20; C07D 401/12; C07D 401/14; C07D 493/04; C07C 247/04
See application file for complete search history.

(56) References Cited

U.S. PATENT DOCUMENTS

| | | |
|---|---|---|
| 5,196,438 A | 3/1993 | Martin et al. |
| 6,436,989 B1 | 8/2002 | Hale et al. |
| 6,514,953 B1 | 2/2003 | Armitage et al. |

FOREIGN PATENT DOCUMENTS

| | | |
|---|---|---|
| EP | 0 432 695 A2 | 6/1991 |
| WO | 99/67254 A2 | 12/1999 |
| WO | 99/67417 A2 | 12/1999 |
| WO | 00/18384 A2 | 4/2000 |

OTHER PUBLICATIONS

Bennett et al.(J. Chem. Soc., Chem. Commun., 1993; p. 737-738).*
Parkes, K.E.B., et al., Studies Toward the Large-Scale Synthesis of the HIV Proteinase Inhibitor Ro 31-8959, Journal of Organic Chemistry, vol. 59, No. 13/16, pp. 3656-3664, XP002011975, ISSN: 0022-3263, Jan. 1, 1994 (9 pages).
Ghosh, Arun K., et al., The Development of Cyclic Sulfolanes as Novel and High-Affinity P2 Ligands for HIV-1 Protease Inhibitors, Journal of Medicinal Chemistry, vol. 37, No. 8, pp. 1177-1188, XP055057710, ISSN: 0022-2623, Apr. 1, 1994 (12 pages).
Tokunaga, M., Asymmetric Catalysis With Water: Efficient Kinetic Resolution of Terminal Epoxides by Means of Catalytic Hydrolysis, Science, vol. 277, No. 5328, pp. 936-938, XP055057541, ISSN: 0036-8075, Aug. 15, 1997 (4 pages).
Brickmann, Kay, et al., Synthesis of Conformationally Restricted Mimetics of [gamma]—Turns and Incorporation into Desmopressin, an Analogue of the Peptide Hormone Vasopressin, Chemistry—A European Journal, vol. 5, No. 8, pp. 2241-2253, XP055057517, ISSN: 0947-6539, Aug. 2, 1999 (13 pages).
Nagumo, Shinji, et al., Intramolecular Friedel-Crafts Type Reaction of Vinyloxiranes Linked to an Ester Group, Tetrahedron, vol. 65, No. 47, pp. 9884-9896, XP055057655, ISSN: 0040-4020, Nov. 1, 2009 (13 pages).

(Continued)

*Primary Examiner* — Valerie Rodriguez-Garcia
(74) *Attorney, Agent, or Firm* — Wood, Herron & Evans, LLP

(57) ABSTRACT

A novel synthetic route to the syn-azido epoxide of formula 5 includes cobalt-catalyzed hydrolytic kinetic resolution of a racemic mixture of the azido-epoxide. Reaction steps include subjecting an allylic alcohol to epoxidation with mCPBA to obtain a racemic epoxy alcohol; ring opening the epoxy alcohol with azide anion to obtain an anti-azido alcohol, which can then be selectively tosylated at the primary alcohol; treating the tosylate with base to obtain the racemic azido-epoxide; and subjecting the racemic azido-epoxide to cobalt-catalyzed hydrolytic kinetic resolution to obtain the syn-azido epoxide of formula 5. The compound of formula 5 may be used as a common intermediate for the asymmetric synthesis of HIV protease inhibitors, such as Amprenavir, Fosamprenavir, Saquinavir, and formal synthesis of Darunavir and Palinavir.

18 Claims, No Drawings

(56) References Cited

OTHER PUBLICATIONS

Reddy, R. Santhosh, et al., Co (III)(salen)-catalyzed HKR of Two Stereocentered Alkoxy- and Azido Epoxides: A Concise Enantioselective Synthesis of (S,S)-reboxetine and (+)-epi-cytoxazone, Chemical Communications, vol. 46, No. 27, p. 5012-5014, XP055057537, ISSN: 1359-7345, Jan. 1, 2010 (3 pages).

Kiran, I.N. Chaithanya, et al., A Concise Enantioselective Synthesis of (+)-goniodiol and (+)-8-methoxygoniodiol via Co-catalyzed HKR of anti-(2SR, 3RS)-3-methoxy-3-phenyl-1, 2-epoxypropane, Tetrahedron Letters, Elsevier, Amsterdam, NL, vol. 52, No. 3, pp. 438-440, XP027558447, ISSN: 0040-4039, Jan. 19, 2011 (3 pages).

Gadakh, Sunita K., et al., Enantioselective Synthesis of HIV Protease Inhibitor Amprenavir Via Co-Catalyzed HKR of 2-(1-azido-2-phenylethyl)oxirane, Tetrahedron: Asymmetry, vol. 23, No. 11-12, pp. 898-903, XP055057475, ISSN: 0957-4166, Jun. 1, 2012 (6 pages).

European Patent Office, International Search Report, International Application No. PCT/IN2013/000021, mailed Apr. 9, 2013 (3 pages).

Council of Scientfic & Industrial Research, Informal Comments in Response to International Search Report Dated Apr. 9, 2013, International Application No. PCT/IN2013/000021, mailed Jun. 10, 2013 (7 pages).

The International Bureau of WIPO, International Preliminary Report on Patentability and Written Opinion of the International Searching Authority, International Application No. PCT/IN2013/000021, mailed Jul. 24, 2014 (8 pages).

Sangwoo Park et al., Efficient Synthesis of 2(S)[1(S)-Azido-2-phenylethyl]oxirane, Bulletin of the Korean Chemical Society, Jan. 25, 2008, pp. 1073-1074, vol. 29, No. 5.

Pierre L. Beaulieu et al., Practical, Stereoselective Synthesis of Palinavir, a Potent HIV Protease Inhibitor, The Journal of Organic Chemistry, Feb. 12, 1997, pp. 3440-3448, vol. 62, No. 11.

* cited by examiner

PROCESS FOR SYNTHESIS OF SYN AZIDO EPDXIDE AND ITS USE AS INTERMEDIATE FOR THE SYNTHESIS OF AMPRENAVIR AND SAQUINAVIR

CROSS-REFERENCE TO RELATED APPLICATIONS

This application is a submission under 35 U.S.C. §371 of International Application No. PCT/IN2012/000827, filed Dec. 18, 2012, which claims priority to Indian Application No. 3731DEL2011, filed Dec. 20, 2011, the disclosures of which are hereby expressly incorporated by reference herein in their entireties.

TECHNICAL FIELD

The invention relates to a novel process for the synthesis of syn-azido epoxide intermediate. Further, the invention relates to short and efficient asymmetric synthesis of HIV protease inhibitors such as amprenavir, fosamprenavir, saquinavir and formal syntheses of darunavir and palinavir via syn azido epoxide, with high enantiomeric excess, as a common intermediate obtained by Cobalt-catalyzed hydrolytic kinetic resolution of racemic anti-(2SR, 3SR)-3-azido-4-phenyl-1,2-epoxybutane (azido-epoxide).

BACKGROUND

The etiologic agent, such as human immunodeficiency virus type 1 and type 2 (HIV-1 and HIV-2), that causes acquired immunodeficiency syndrome (AIDS), encodes for a specific aspartyl proteinase (HIV-protease). The inhibition of HIV-proteases by peptidomimetic structures incorporating a hydroxyethylamine (HEA) isostere offers a promising approach for the treatment of AIDS.

Many potent drugs, such as amprenavir, fosamprenavir, saquinavir, darunavir, and palinavir which belong to the HEA class, have complex structures equipped with multiple stereogenic centers. Due to the potential biological importance of these HIV inhibitors, considerable effort has been directed at methods for their synthesis.

HIV protease inhibitors have been developed as some of the most promising chemotherapeutic agents for the treatment of AIDS, and they exhibit complex structures equipped with multiple steriogenic centers. Thus, synthetic organic chemists have been attracted towards development of an efficient and practical synthetic route for these inhibitors. Amprenavir 1 developed by Vertex and GlaxoSmithKline, is an HIV protease inhibitor that was approved by the FDA in 1999. Fosamprenavir 2, launched in 2003, is a prodrug with increased therapeutic efficacy.

Several publications have disclosed the synthesis of HIV protease inhibitors, and some relevant documents are mentioned below.

WO 2000/018384 discloses a pharmaceutical combination comprising (S)-2-ethyl-7-fluoro-3oxo-3,4-dihydro-2H-quinoxaline-1-carboxylic acid isopropyl ester or a physiologically functional derivative thereof and 4 amino 4-amino-N-((2-syn,3S)-2-hydroxy-4-phenyl-3((S)-tetrahydrofuran-3-yloxycarbonylamino)butyl)-N-isobutylbenzenesulfonamide (amprenavir) or a physiologically functional derivative thereof.

U.S. Pat. No. 6,436,989 discloses fosamprenavir calcium and other salts of fosamprenavir, such as sodium, potassium, and magnesium, their pharmaceutical compositions, and methods of treating HIV infection and inhibiting aspartyl protease activity in a mammal. U.S. Pat. No. 6,514,953 discloses polymorphic Form I of fosamprenavir calcium, its pharmaceutical composition, and its method of use for treatment of an HIV infection, wherein the process for the preparation of a fosamprenavir or its salts comprises reacting a compound of formula (II) with a phosphorylating agent and further reduction.

Further preparation of saquinavir is described in U.S. Pat. No. 5,196,438 and also European Patent No. EP432695, wherein (3S)-1,2,3,4-tetrahydroisoquinoline-3-carboxylic acid was hydrogenated with hydrogen gas at higher pressure in presence of Rhodium on carbon as catalyst using 90% acetic acid. The final step involves treatment of (2S)—N-[(1S,2R)-3-[(3S,4aS,8aS)-3-(tert-butylcarbamoyl)-octahydro-1H-isoquinolin-2-yl]-1-benzyl-2-hydroxy-propyl]-2-amino-butanediamide with quinaldic acid in presence of hydroxybenzotriazole and dicyclohexylcarbodiimide using N-ethylmorpholine as base.

Also, the preparation of darunavir is reported in WO 99/67417 and WO 99/67254.

The multistep stereoselective synthesis of palinavir, a potent HIV protease inhibitor, is disclosed in *J. Org. Chem.*, 1997, 62 (11), pp 3440-3448 by Pierre L. Beaulieu et al.

Although several methods have been tried for the syntheses of HIV protease inhibitors, some of them require chiral auxiliaries or use of chiral building blocks and exotic reagents, involve longer reaction sequences, and expensive catalysts coupled with low enantiomeric excess, making the processes non feasible industrially.

Additionally, several synthetic approaches of azido epoxide (5), the key chiral building block in the synthesis of HEA-based HIV protease inhibitors, have been reported in the literature.

An article titled "Efficient Synthesis of 2(S)-[1(S)-Azido-2-phenylethyl]oxirane" by Sangwoo Park, Sangmi Lee, and Ho-Jung Kang in Bull. Korean Chem. Soc. 2008, Vol. 29, No. 5 1073, discloses efficient synthesis of 2(S)-[1(S)-azido-2-phenylethyl]oxirane (1) from acetonide 2 as a starting material by 9 steps with two purification steps at alcohol 3 and oxirane 1, respectively, in overall yield of 48%, providing an expedient route to the facile, practical, and large-scale production of the desired epoxide 1 and other related structural motiffs from the cheaper D-isoascorbic acid.

WO 99/67254 provides a retroviral protease-inhibiting compound represented by formula (I) or a pharmaceutically acceptable salt thereof, a prodrug, or an ester thereof, wherein A is a group of formula (II), (III), (IV), or (V);

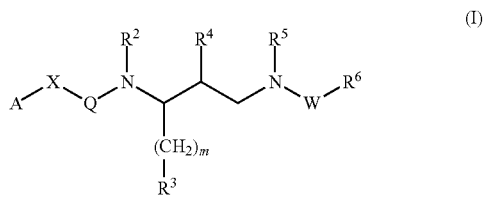

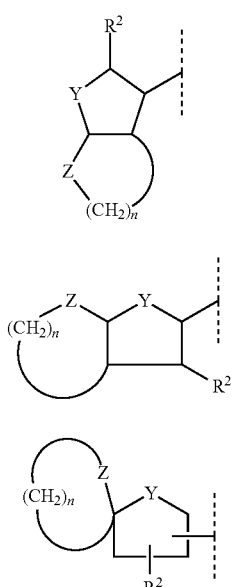

(II)

(III)

(IV)

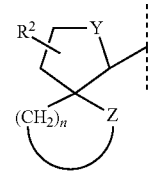

(V)

The said patent application further provides a method of synthesizing the multidrug-resistant, retroviral protease-inhibiting compounds, such as for example, ritonavir, saquinavir, indinavir, amprenavir, AZT, ddl, ddC, d4T, 3TC, ABV (abacavir), DLV (delaviridine), and PFA (foscarnet), of the present invention.

The said synthesis method is generally illustrated in FIG. 4 of WO 99/67254, wherein a compound of Formula (I) is synthesized in several steps starting from azidoepoxide (i), amine (ii) is nucleophilically added to azidoepoxide (i) to afford aminoalcohol (iii), which is then reacted with intermediate (iv), which can be displaced by the amine of aminoalcohol (iii), to provide azide (v); reduction of azide (v), provides intermediate (vi), which is subsequently coupled with activated bicyclic ligand (vii) gives compound (I)(c.f. below scheme).

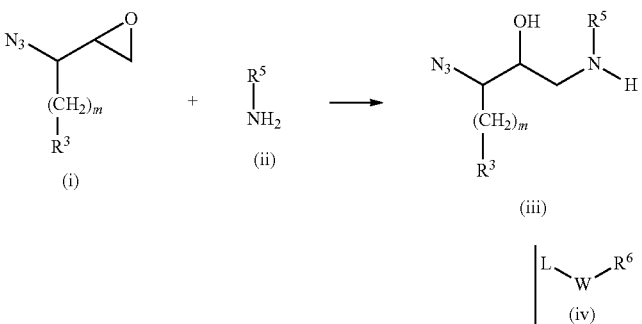

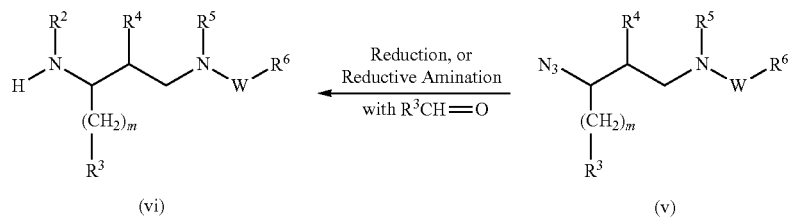

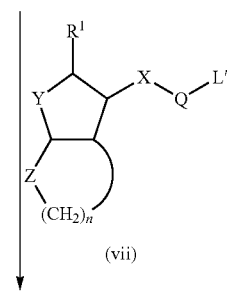

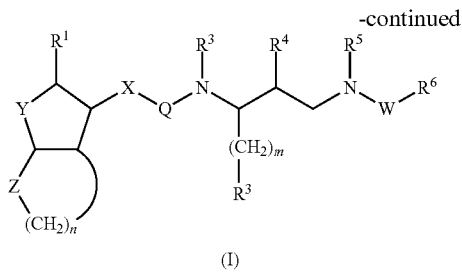

(I)

However, the few methods that relate to the synthesis of the azido epoxide compound suffer from limitations, such as the use of chiral building blocks, introduction of chirality in the early stages, long reaction sequences, the use of expensive catalysts, low % ee, and so on, and hence are not amenable for scale-up studies.

Therefore, there is a need in the art to provide an efficient method of synthesizing azido epoxide compound (5), which can be further used to provide an efficient synthetic method for the preparation of HIV protease inhibitors, such as amprenavir, fosamprenavir, saquinavir, darunavir, palinavir, and their structural analogues, that proceed with high enantioselectivities (99% ee), in a concise manner.

Accordingly, the present invention provides a new synthetic route for the preparation of racemic azido epoxide (5) from commercially available allylic alcohol.

Accordingly, the present inventors have further developed a new synthetic route for the preparation of HIV protease inhibitors, comprising hydrolytic kinetic resolution (HKR) of a racemic azido epoxide as a key step to obtain the HIV protease inhibitors in high yield and high enantioselectivity. Further, the process developed by the inventor is efficient, cost effective as it involves simple organic reagents and water, and industrially viable, as well as socially important.

OBJECT OF INVENTION

In view of above, the objective of the invention is to provide a short, enantioselective synthesis of HIV protease inhibitors, such as amprenavir, saquinavir, fosamprenavir, and a formal synthesis of darunavir and palinavir, with high enantioselectivities (99% ee), via Co-catalyzed hydrolytic kinetic resolution (HKR) of racemic anti-(2SR,3SR)-3-azido-4-phenyl-1,2-epoxybutane, i.e racemic azido-epoxide, as chiral-inducing key reactions, wherein the route of synthesis of racemic anti-(2SR,3SR)-3-azido-4-phenyl-1,2-epoxybutane, i.e racemic azido-epoxide, is also through a novel route.

SUMMARY

Accordingly, the present invention provides an enantioselective synthesis of syn azido epoxide of formula (+)-5

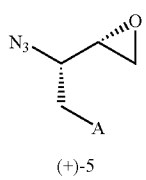

(+)-5 wherein, A is an unsubstituted aryl group or substituted aryl group, the substituents being selected from (C1-C8) alkyl, aryl, arylalkyl, halo, and (C1-C8) alkoxy, said synthesis comprising i) subjecting an allylic alcohol to epoxidation with m-chlorobenzoic acid (mCPBA) to obtain a racemic epoxy alcohol;
ii) ring opening of the epoxide with azide anion in the presence of a Lewis acid to produce an anti-azido alcohol, followed by selective tosylation of the primary alcohol to afford a tosylate;
iii) treating the tosylate with a base to obtain a racemic azido epoxide; and
iv) subjecting the racemic azido epoxide to hydrolytic kinetic resolution to obtain a corresponding 1,2-diol and the syn azido epoxide, followed by isolating the syn azido epoxide with enantiomeric purity>98%.

In an embodiment of the invention, the allylic alcohol is aryl substituted or unsubstituted butene alcohol.

In another embodiment of the invention, the Lewis acid is selected from the group consisting of BF3, anhydrous AlCl3, PF5, TiCl4, Ti(OiPr)4, zinc bromide, and cerium(III)Chloride.

In still another embodiment of the invention, the source of azide anion is selected from inorganic azide, such as sodium azide, chlorine, bromine, and iodine azides, or organic azide, such as tosyl azide, and trimethylsilyl azide, in a suitable organic solvent.

In a further embodiment of the invention, the hydrolytic kinetic resolution is carried out in the presence of (S,S)-Co (Salen)acetate complex in a concentration in the range of 0.2-0.8 mol %, in suitable organic solvent.

Accordingly, the present invention also provides an enantioselective synthesis of HIV protease inhibitors from the syn azido epoxide of formula (+)-5, comprising converting said syn azido epoxide to said HIV protease inhibitors, wherein said syn azido epoxide is prepared by a process comprising:

i) subjecting an allylic alcohol to epoxidation with m-chlorobenzoic acid (mCPBA) to obtain a racemic epoxy alcohol;
ii) ring opening of the epoxide with azide anion in the presence of a Lewis acid to produce an anti-azido alcohol, followed by selective tosylation of the primary alcohol to afford a tosylate;
iii) treating the tosylate with a base to obtain a racemic azido epoxide; and
iv) subjecting the racemic azido epoxide to hydrolytic kinetic resolution to obtain a corresponding 1,2-diol and the syn azido epoxide, followed by isolating the syn azido epoxide with enantiomeric purity of >98%.

In an embodiment of the invention, the HIV protease inhibitors are selected from amprenavir, fosamprenavir, saquinavir, darunavir, and palinavir.

In another embodiment of the invention, the allylic alcohol is aryl substituted or unsubstituted.

In yet another embodiment of the invention, the Lewis acid is selected from the group consisting of BF3, anhydrous AlCl3, PF5, TiCl$_4$, Ti(OiPr)$_4$, zinc bromide and cerium(III) Chloride.

In still another embodiment of the invention, the source of azide anion is selected from inorganic azide, such as sodium azide, chlorine, bromine, and iodine azides, or organic azide, such as tosyl azide, and trimethylsilyl azide, in suitable organic solvent.

In a further embodiment of the invention, the hydrolytic kinetic resolution is carried out in the presence of (S,S)-Co (Salen)acetate complex in a concentration in the range of 0.2-0.8 mol %, in suitable organic solvent.

In a further embodiment of the invention, the conversion of the syn azido epoxide into amprenavir comprises steps of (i) subjecting the syn azido epoxide to a regiospecific ring opening with iso butyl amine to give an azido alcohol; ii) converting the azido alcohol into its nosylate to obtain an azido nosylate; iii) converting the azido nosylate into amprenavir by using standard sequence of reactions, such as azide reduction, condensation with (S)-3-hydroxytetrahydrofuran, and reduction of the nitro group to an amine functionality.

In one embodiment of the invention, the nosylating agent may be selected from, para-nitrobenzenesulfonyl isocyanate, para-nitrobenzenesulfonyl anhydride, or para-nitrobenzenesulfonyl chloride.

In still another embodiment of the invention, the reducing agent may be selected from $SnCl_2$, $LiAlH_4$, or any suitable salt of Li, Al, Mg, Al, Fe, Cu, Ag, or Na in solvent.

In a further embodiment of the invention, the base may be selected from inorganic base, such as alkali or alkaline metal oxide, hydroxides, carbonates, bicarbonates, hydride, particularly $K_2CO_3$, NaOH, Na2CO3, $NaHCO_3$, CaOH, KOH, $CsCO_3$, or an organic base, alkyl amine, arylamine, heterocylic amine, such as branched or linear alkyl (n-butyl, triethyl, trimethyl, or sec-propyl amines), or aniline, pyridine, pyrollidine, or amino acid, either alone or mixtures thereof in suitable solvent.

In a further embodiment of the invention, a suitable organic solvent may be selected from the group consisting of polar aprotic solvents, such as DCM, THF, ethyl acetate, acetone, DMF, acetonitrile, and DMSO, or polar protic solvents, such as lower alcohol, particularly (C1-C6) alkyl alcohol, water, and acetic acid, or non-polar solvents, such as hexane, benzene, toluene, chloroform, petroleum ether, 1,4-dioxane, and heptane, either alone or in mixtures thereof.

In a further embodiment of the invention, the syn azido epoxide is converted to saquinavir by treating the same with [(3S)-(3α,4αβ,8αβ)]-N-(tert-butyl)decahydro-3-isoquinolinecarboxamide in presence of silica gel (230-400, 6 Å mesh) in organic solvent to yield 2-(3(S)-Azido-2(R)-hydroxy-4-phenylbutyl)-N-tert-butyldecahydro-(4aS,8aS) isoquinoline-3(S)-carboxamide, which is converted into sequinavir by known methods.

Abbreviations:
Co-catalyzed HKR: Cobalt catalyzed hydrolytic kinetic resolution

DESCRIPTION OF THE INVENTION

The invention will now be described in detail in connection with certain preferred and optional embodiments, so that various aspects thereof may be more fully understood and appreciated.

In the preferred embodiment, the present invention provides an efficient route for the synthesis of the HIV protease inhibitors selected from the group consisting of amprenavir (1), fosamprenavir (2), saquinavir (3), darunavir (4), and palinavir (6) based on hydrolytic kinetic resolution (HKR) of racemic azido epoxide, also known as racemic azido oxirane, as a common key intermediate.

In one embodiment, the invention provides an asymmetric synthesis for the preparation of the key intermediate, i.e., two stereocentered azido epoxide (+)-5, from commercially available allylic alcohol, as depicted in scheme 1.

The syn azido epoxide (+)-5 is chemically known as 2(S)-[1'(S)-azido-2-phenylethyl]oxirane. The enantioselective synthesis of two stereocentered azido epoxide (+)-5 comprises steps of
i) subjecting allylic alcohol (7) to epoxidation with m-chlorobenzoic acid (mCPBA) to obtain racemic epoxy alcohol (8);
ii) ring opening of epoxide (8) with azide anion in presence of a Lewis acid to produce the anti-azido alcohol (9), followed by selective tosylation of the primary alcohol to afford tosylate (10);
iii) treating the tosylate with base to obtain racemic azido epoxide (11);
iv) subjecting racemic azido epoxide (11) to hydrolytic kinetic resolution to obtain the corresponding 1,2-diol (12) and azido epoxide (+)-5, and subsequent separation, giving (+)-5 in high enantiomeric purity.

Scheme 1: Synthesis of syn azido epoxide: (+)-5

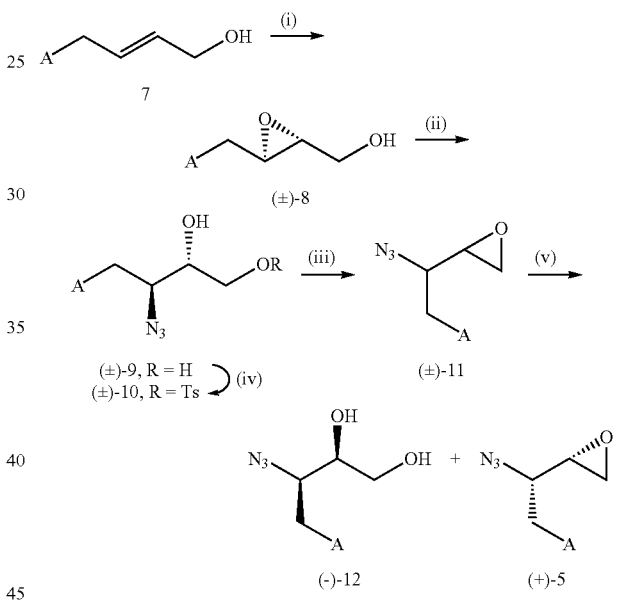

wherein A is an unsubstituted aryl group or substituted aryl group, the substituents being selected from (C1-C8) alkyl, aryl, arylalkyl, halo, and (C1-C8) alkoxy.

In scheme 1, allylic alcohol 7 is prepared in quantitative yield by known techniques, particularly from phenylacetaldehyde in two steps: (i) a Wittig-Horner reaction in presence of benzaldehyde, and ethyl triphenylphosphoranylidene acetate in suitable solvent at (90° C.); and (ii) a selective ester reduction in the presence of LiAlH4, catalytic AlCl3, dry ether, 0° C.). The allylic alcohol is particularly selected from (E)-4-phenyl but-2-en-1-ol, wherein the phenyl group is either substituted or unsubstituted.

The alcohol (7) is then subjected to epoxidation with m-chlorobenzoic acid (mCPBA) to obtain racemic epoxy alcohol (8) in more than 85% yield. The Lewis acid-catalyzed ring opening of epoxide (8) with azide anion produces the anti-azido alcohol (9) (more than 95% yield) in a highly regioselective manner (regioisomer distribution: 27:1). In the ring opening step, the Lewis acid is selected from the group consisting of BF3, anhydrous AlCl3, PF5, $TiCl_4$, $Ti(OiPr)_4$, zinc bromide, cerium(III)chloride, and other metal salts. The azide anion can be obtained from inorganic azide, such as sodium azide, chlorine, bromine, and iodine azides, or organic azide, such as tosyl azide, trimethylsilyl azide and the like, in a suitable organic solvent. The temperature is maintained above 50° C. to reduce the reaction time; preferably the temperature is in the range of 60° C.-80° C.

Further the desired regioisomer (9) is separated by column chromatography and transformed into racemic azido epoxide (11) by selective tosylation of the primary alcohol, followed by a base treatment to obtain epoxide (11) with a yield of more than 90%. The racemic azido epoxide (11) is subsequently subjected to HKR with the (S,S)-salen Co(OAc) complex (0.2-0.8 mol %) in suitable organic solvent and H$_2$O (0.3 to 0.6 equiv), which affords the corresponding diol, i.e. (2R,3R)-3-azido-4-phenylbutane-1,2-diol (12), and syn azido-epoxide, i.e. 2(S)-[1'(S)-azido-2-phenylethyl]oxirane (5), with high yield and enantiomeric purity, particularly more than 98% ee. The desired intermediate compound, azido epoxide (+)-5, is separated from diol (−)-12 by a simple column chromatography technique.

The regioselective toslylation is carried out in presence of dibutyltin oxide (DBTO), the tosylating agent being selected from tosyl chloride, tosyl anhydride, and p-toluenesulfonyl acid, with addition of a dichloromethane solution of a catalytic amount of 4-dimethylaminopyridine (DMAP) and base.

The base is selected from inorganic base, such as alkali or alkaline metal oxide, hydroxides, carbonates, bicarbonates, hydride, and the like, particularly K$_2$CO$_3$, NaOH, Na2CO$_3$, NaHCO$_3$, CaOH, KOH, CsCO$_3$, either alone or in combination thereof. However, the organic base is not limited to alkyl amine, arylamine, or heterocylic amine, such as branched or linear alkyl, e.g., n-butyl, triethyl, trimethyl, or sec-propyl amines, aniline, pyridine, pyrollidine, amino acid, and mixtures thereof in lower alcohol, such as ethanol, methanol, propanol, or butanol. The tosylation is preferably carried out at low temperature.

Additionally, the HKR uses water as the only reagent, no added solvent, and low loading of recyclable chiral cobalt-based salen complexes to afford the terminal epoxides and 1,2-diol in high yield and high enantiomeric excess, with no effluent generated. Also the instant method is easy to perform at higher scales (kgs).

In another embodiment, the enantioenriched syn-azido epoxide thus obtained is subjected to regioselective azide displacement of epoxy alcohol and insertion of a heterocyclic moiety, as shown in schemes 2 to 5, to obtain the desired HIV protease inhibitors, such as amprenavir 1, fosamprenavir 2, saquinavir 3, darunavir 4, and palinavir 6, in high yield and enantiomeric purity of >98%, in a concise manner.

In an embodiment, the present invention provides an asymmetric synthesis of amprenavir (1), from the key intermediate, syn-azido epoxide (+)-5, which is represented by scheme 2, Scheme 2: Synthesis of Amprenavir: (1)

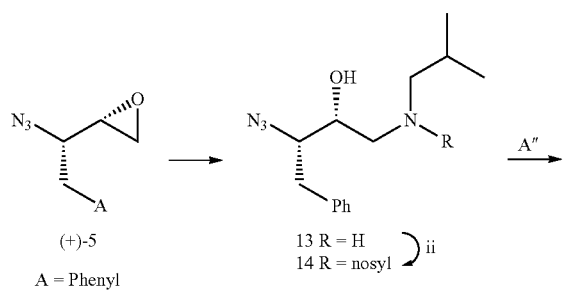

(+)-5

A = Phenyl

13 R = H
14 R = nosyl  } ii

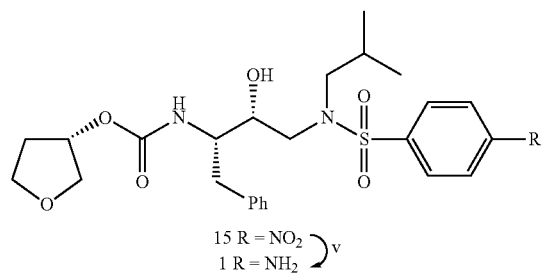

15 R = NO$_2$  } v
1 R = NH$_2$

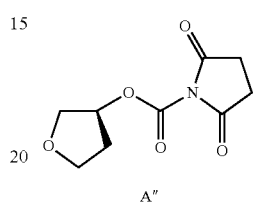

A″

In accordance with scheme 2, compound 5 is subjected to a regiospecific ring opening with isobutylamine in suitable solvent to give azidoalcohol 13, which is subsequently protected as its nosylate 14 in the presence of base and organic solvent at lower temperature. The nosylating agent is selected from, para-nitrobenzenesulfonyl isocyanate, para-nitrobenzenesulfonyl anhydride, or para-nitrobenzenesulfonyl chloride.

Azido nosylate 14 was finally transformed into amprenavir 1 in three steps with an overall yield of more than 90% by following a standard sequence of reactions: (i) azide reduction in presence of triphenylphosphine and suitable organic solvent; (ii) condensation with N-hydroxysuccinimidyl carbonate of (S)-3-hydroxytetrahydrofuran (A″) at ambient condition in the presence of a strong base; and (iii) reduction of the nitro group to an amine functionality in the presence of a reducing agent, such as SnCl$_2$, LiAlH$_4$, or any suitable salt of Li, Al, Mg, Al, Fe, Cu, Ag, or Na, in solvent at high temperature (50-80° C.).

In another embodiment, the invention provides a synthesis of fosamprenavir, which is a phosphonooxy salt of amprenavir and can be prepared by treatment of the amprenavir synthesized by the instant process with phosphoric acid (c.f. scheme 3 below). Treatment with phosphoric acid is a known technique used in the preparation of protease inhibitors.

Scheme 3: Synthesis of Fosamprenavir (2):

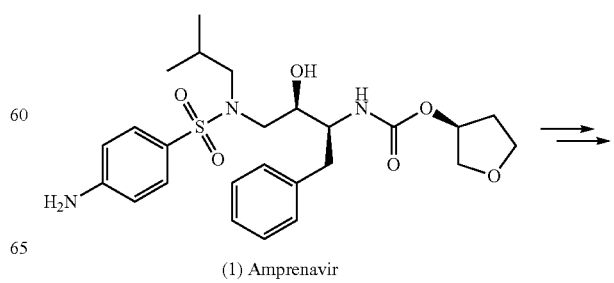

(1) Amprenavir

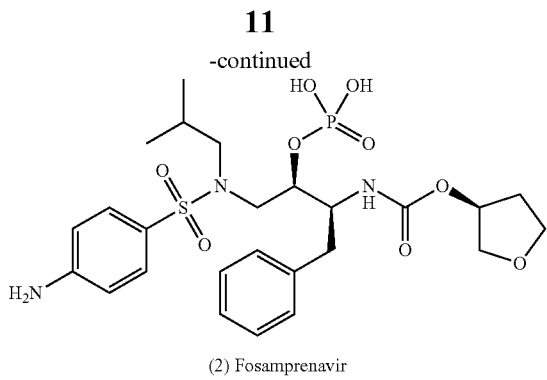

(2) Fosamprenavir

In another embodiment, the invention provides a synthesis of saquinavir (3) from the key intermediate azido-epoxide. The synthesis comprises treatment of azido epoxide (+)-5 with [(3S)-(3α,4αβ,8αβ)]-N-(tert-butyl)decahydro-3-isoquinolinecarboxamide in the presence of silica gel (230-400, 6 Å mesh) in organic solvent to give more than 85% yield of the key azido alcohol (16) in a highly regioselective fashion. The transformation of 16 into saquinavir 3 is known in the literature. The synthesis of saquinavir is represented below in scheme 4.

Scheme 4: Synthesis of Squinavir (3):

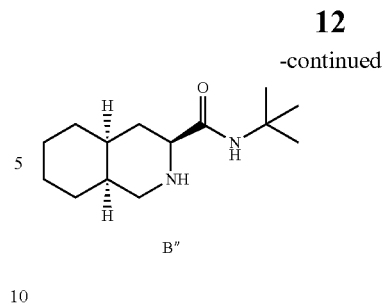

B''

In yet another embodiment, the formal synthesis of darunavir is provided, starting with syn azido-epoxide (+)-5 prepared by hydrolytic kinetic resolution (HKR) of the racemic azido epoxide according to the invention. The synthesis of darunavir is represented below in scheme 5.

Scheme 5: Synthesis of Darunavir (4);

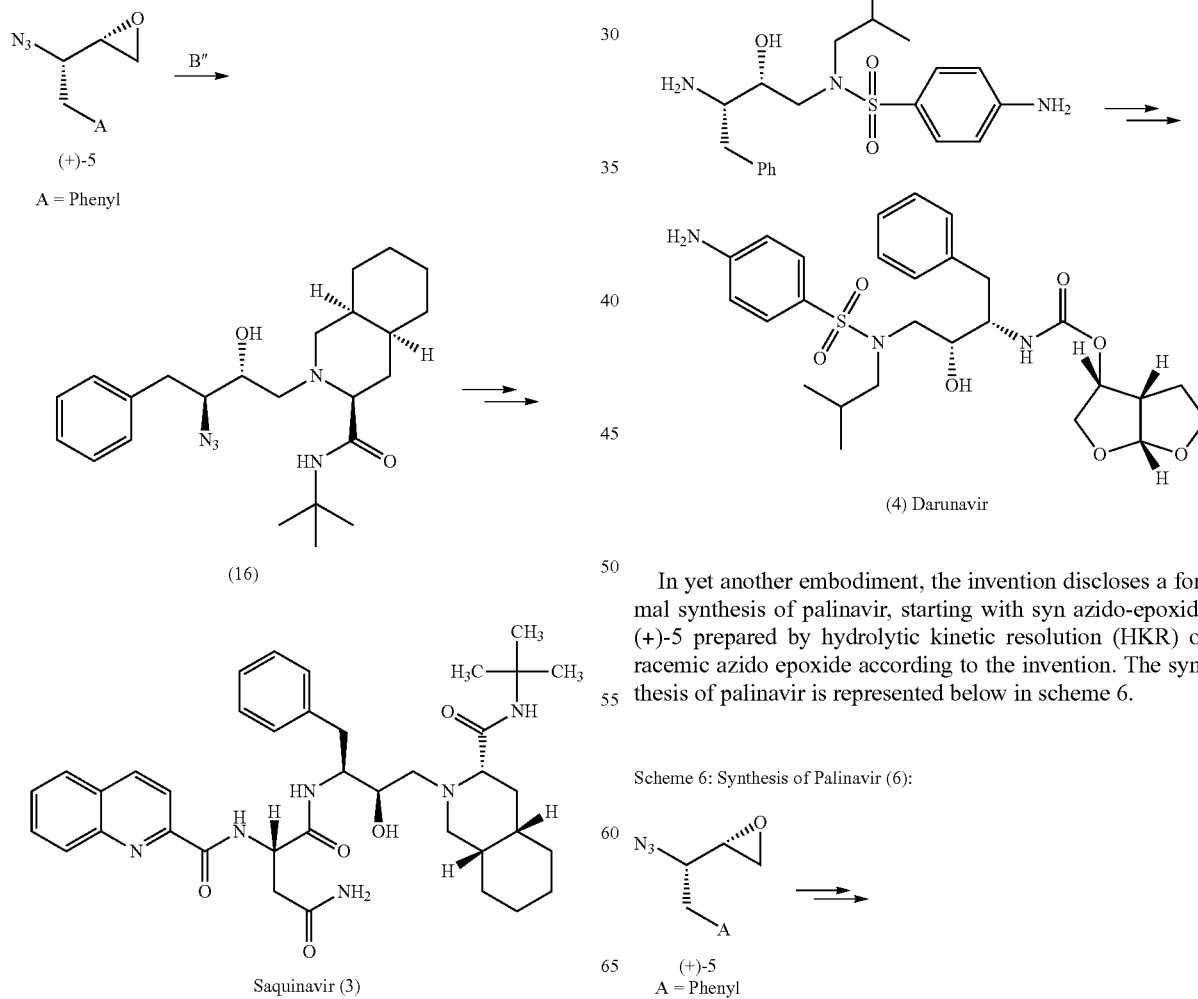

(4) Darunavir

In yet another embodiment, the invention discloses a formal synthesis of palinavir, starting with syn azido-epoxide (+)-5 prepared by hydrolytic kinetic resolution (HKR) of racemic azido epoxide according to the invention. The synthesis of palinavir is represented below in scheme 6.

Scheme 6: Synthesis of Palinavir (6):

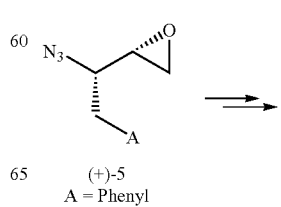

(+)-5
A = Phenyl

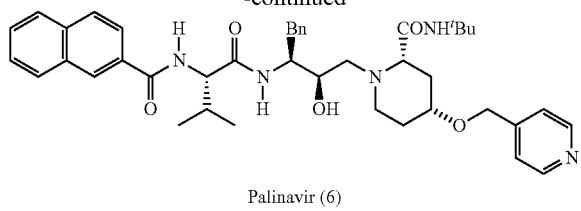

Palinavir (6)

The organic solvent is selected from the group consisting of solvents, such as polar aprotic solvents including DCM, THF, Ethyl acetate, acetone, DMF, acetonitrile, and DMSO; polar protic solvents, such as lower alcohol including (C1-C6) alkyl alcohol, water, and acetic acid; and non-polar solvents such as hexane, benzene, toluene, chloroform, petroleum ether, 1,4-dioxane, and heptane, either alone or mixtures thereof.

Additionally the purification or separation of the crude product can be accomplished by known techniques, viz. extraction; column chromatography in a suitable organic solvent with the aid of instruments such as TLC, HPLC, GC, and mass spectroscopy; distillation; crystallization; and derivatization.

The following examples, which include preferred embodiments, will serve to illustrate the practice of this invention, it being understood that the particulars shown are by way of examples and for purpose of illustrative discussion of preferred embodiments of the invention only and are not limiting of the scope of the invention.

EXAMPLES

Materials and Methods

The solvents were purified and dried by standard procedures prior to use. Optical rotations were measured using sodium D line on a JASCO-181 digital polarimeter. IR spectra were recorded on a Thermo Scientific-Nicolet 380 FT-IR and absorption is expressed in $cm^{-1}$. $^1H$ NMR and $^{13}C$ NMR spectra were recorded on Brucker AC-200 spectrometer unless mentioned otherwise. Elemental analysis was carried out on a Carlo Erba CHNS-O analyzer. Purification was carried out using column chromatography (60-120 mesh). Enantiomeric excesses were determined on Agilent HPLC instrument equipped with a suitable chiral column.

Example 1

Synthesis of (E)-Ethyl 4-phenylbut-2-enoate

To a stirred solution of phenyl acetaldehyde (7.0 g, 58.3 mmol) in benzene (150 mL) was added (ethoxycarbonylmethylene)triphenylphosphorane (22.3 g, 64.1 mmol) and the resulting mixture heated under reflux for 6 h. After the reaction was complete, solvent was removed under reduced pressure to provide the crude product, which was then purified by column chromatography over silica gel using petroleum ether/EtOAc (19:1) to give α,β unsaturated ester 6 (10.6 g, 96%) as a colorless oil. IR: ($CHCl_3$, $cm^{-1}$): $v_{max}$ 699, 1041, 1098, 1158, 1270, 1301, 1669, 1721, 1782, 2858, 2984; $^1H$ NMR (200 MHz, $CDCl_3$): δ 1.28 (t, J=7.1 Hz, 3H), 3.23 (d, J=6.8 Hz, 2H), 4.17 (q, J=7.0 Hz, 2H), 6.21-6.35 (m, 1H), 6.48 (d, J=15.6 Hz, 1H), 7.14-7.37 (m, 5H); $^{13}C$ NMR (50 MHz, $CDCl_3$): δ 14.2, 38.4, 60.1, 122.4, 126.7, 128.6, 128.7, 137.6, 147.1, 166.2; Anal. Calcd for $C_{12}H_{14}O_2$: C, 75.76; H, 7.42. Found: C, 75.65; H, 7.41%.

Example 2

Synthesis of (E)-4-Phenylbut-2-en-1-ol (7)

To a stirred suspension of $LiAlH_4$ (2.4 g, 63.1 mmol) in dry $Et_2O$ (60 mL) at 0° C. under nitrogen atmosphere was added dropwise a solution of anhydrous $AlCl_3$ (1.7 g, 12.6 mmol) in dry $Et_2O$ (30 mL). The reaction mixture was stirred at the same temperature for 30 min. To this stirred suspension, ester obtained in example 1 (8.0 g, 42.1 mmol) in dry $Et_2O$ (30 mL) was added dropwise over a period of 15 min and the resulting mixture stirred at 0° C. for 1 h. Then it was quenched with ice-water and filtered through celite and the residue was washed with ethyl acetate (3×30 mL). The combined organic layer was dried over anhydrous $Na_2SO_4$, concentrated, and the crude product was purified by column chromatography using petroleum ether/EtOAc (4:1) to afford the pure allylic alcohol 7 (5.4 g, 87%) as a colorless oil. IR: ($CHCl_3$, $cm^{-1}$): $v_{max}$ 694, 744, 966, 1049, 1107, 1364, 1454, 2857, 2932, 3385; $^1H$ NMR (200 MHz, $CDCl_3$): δ 1.22 (br s, 1H), 3.38 (d, J=6.4 Hz, 2H), 4.12 (t, J=4.8 Hz, 2H), 5.62-5.93 (m, 2H), 7.15-7.32 (m, 5H); $^{13}C$ NMR (50 MHz, $CDCl_3$): δ 36.4, 61.9, 126.0, 126.3, 127.2, 128.5, 132.7, 137.2; Anal. Calcd for $C_{10}H_{12}O$: C, 81.04; H, 8.16. Found: C, 81.02; H, 8.15%.

Example 3

Synthesis of (3-Benzyloxiran-2-yl) methanol (8)

To a solution of allylic alcohol 7 (5.0 g, 33.7 mmol) in dry $CH_2Cl_2$ (60 mL) at 0° C. was added m-chloroperbenzoic acid (8.7 g, 50.6 mmol) in small portions. The resulting solution was stirred for 8 h until complete consumption of starting materials (the progress of the reaction was monitored by TLC). The reaction mixture was quenched with water and the aqueous layer was extracted with $CH_2Cl_2$ (3×30 mL). The organic layer was washed with aq. 10% solution of $NaHCO_3$ (15 mL). The combined organic layer was dried over anhydrous $Na_2SO_4$, and the solvent was removed under reduced pressure. The crude product was purified by column chromatography over silica gel using petroleum ether/EtOAc (4:1) to give the corresponding epoxide 8 (4.8 g, 88%) as a viscous gum. IR: ($CHCl_3$, $cm^{-1}$): $v_{max}$ 700, 991, 1028, 1055, 1106, 1452, 2921, 3404; $^1H$ NMR (200 MHz, $CDCl_3$): δ 2.88-2.99 (m, 3H), 3.17-3.23 (m, 1H), 3.57-3.72 (m, 1H), 3.85-3.95 (m, 1H), 7.18-7.34 (m, 5H); $^{13}C$ NMR (50 MHz, $CDCl_3$): δ 34.2, 67.1, 78.9, 87.5, 125.5, 127.5, 128.4, 140.8; Anal. Calcd for $C_{10}H_{12}O_2$: C, 73.15; H, 7.37. Found: C, 73.25; H, 7.47%.

Example 4

Synthesis of 3-Azido-4-phenylbutane-1,2-diol (9)

A mixture of freshly distilled $Ti(O^iPr)_4$ (9.5 mL, 32.1 mmol) and $TMSN_3$ (8.4 mL, 64.1 mmol) was refluxed in dry benzene (20 mL) under nitrogen for 5 h until the solution became clear. To this was added a solution of the epoxy alcohol 8 (3.5 g, 21.3 mmol) in 40 mL dry benzene. The resulting mixture was heated under reflux for 15 min, cooled to room temperature and the solvent was removed in vaccuo. The concentrate was diluted with 20 mL of diethyl ether and treated with 15 mL of aq. 5% $H_2SO_4$. The aqueous layer was extracted with $CH_2Cl_2$ and the combined organic layers were dried over anhydrous $Na_2SO_4$ and concentrated to afford the crude product, which was purified by column chromatography using petroleum ether:EtOAc (3:2) to give azido diol 9 (4.2 g, 96%) as a colorless solid. mp 80-81° C. (lit.[10] mp 80.5-82° C.); IR: (CHCl$_3$, cm$^{-1}$): $\nu_{max}$ 696, 753, 1039, 1106, 1242, 1554, 2105, 2923, 2960, 3280; $^1$H NMR (200 MHz, CDCl$_3$): δ 1.79 (t, J=5.3 Hz, 1H), 2.47 (d, J=5.2 Hz, 1H), 2.80 (dd, J=14.2, 8.6 Hz, 1H), 3.02 (dd, J=14.1, 4.2 Hz, 1H), 3.59-3.81 (m, 4H), 7.24-7.32 (m, 5H); $^{13}$C NMR (50 MHz, CDCl$_3$): δ 37.0, 63.2, 65.6, 73.2, 126.9, 128.7, 129.3, 137.2; Anal. Calcd for C$_{10}$H$_{13}$N$_3$O$_2$: C, 57.96; H, 6.32; N, 20.28. Found: C, 57.85; H, 6.28; N, 20.22%.

Example 5

Synthesis of 2-(1-Azido-2-phenylethyl) oxirane (11)

A mixture containing dry Et$_3$N (4.0 mL, 28.9 mmol), Bu$_2$SnO (72 mg, 2 mol %), and N,N-Dimethyl-4-aminopyridine (177 mg, 10 mol %) was added to a solution of azido diol 9 (3 g, 14.5 mmol) in dry CH$_2$Cl$_2$ (40 mL) at 0° C. Solid p-toluene sulfonyl chloride (2.9 g, 15.9 mmol) was then added to the reaction mixture. The resulting mixture was allowed to stir at room temperature for 3 h. It was then diluted with water (10 mL) and extracted with dichloromethane (3×20 mL). The organic phase was washed with brine solution, dried over anhydrous Na$_2$SO$_4$ and concentrated in vacuo to give the crude product 10 (5.0 g), which was used in the next step without purification. To a solution of tosylate 10 (3.0 g, 8.3 mmol) in methanol (25 mL) was added K$_2$CO$_3$ (2.3 g, 16.6 mmol) at 0° C. and the resulting mixture was stirred at 25° C. for 1 h. After the completion of the reaction (monitored by TLC), solvent was evaporated and the residue was extracted with diethyl ether (3×20 mL). The combined ether layer was dried over anhydrous Na$_2$SO$_4$ and concentrated to give the crude product, which was then purified by column chromatography over silica gel using petroleum ether/EtOAc (19:1) to give the azido epoxide 11 (1.5 g) as a colorless liquid (90% over two steps). IR: (CHCl$_3$, cm$^{-1}$): $\nu_{max}$ 701, 760, 930, 1082, 1216, 1455, 1496, 2109, 2401, 2927, 3020; $^1$H NMR (200 MHz, CDCl$_3$): δ 2.79-2.86 (m, 3H), 2.94 (dd, J=13.9, 4.6 Hz, 1H), 3.01-3.07 (m, 1H), 3.51-3.61 (m, 1H), 7.22-7.37 (m, 5H); $^{13}$C NMR (50 MHz, CDCl$_3$): δ 38.2, 45.0, 52.9, 63.6, 126.9, 128.5, 129.3, 136.5; Anal. Calcd for C$_{10}$H$_{11}$N$_3$O: C, 63.48; H, 5.86; N, 22.21. found: C, 63.58; H, 5.55; N, 22.19%.

Example 6

Synthesis of 2(S)-[1'(S)-azido-2-phenylethyl]oxirane (5)

To a solution of (S,S)-Co-complex (43 mg, 0.1 mmol) in toluene (4.0 mL) was added acetic acid (40 mg, 7.3 mmol). It was allowed to stir at 0° C. in open air for 30 min over which time the color of the solution changed from orange-red to a dark brown. It was then concentrated in vaccuo to obtain the Co-salen complex as brown-colored solid. To a solution of Co-salen complex (16 mg, 0.5 mol %) and azido epoxide 11 (1.0 g, 5.3 mmol) in THF (0.5 mL) at 0° C. was added H$_2$O (46 mg, 2.6 mmol) dropwise over 5 min. The reaction mixture was allowed to warm to 25° C. and stirred for 14 h. After completion of reaction (monitored by TLC), solvent was removed in vaccuo. The crude product was purified by column chromatography over silica gel. Solvent system: petroleum ether:EtOAc (19:1) for chiral azido epoxides 5 (480 mg, 48%) and petroleum ether:EtOAc (3:2) for chiral azido diol 12 (537 mg, 49%). [α]$^{20}$$_D$: +13.1 (c=1, CHCl$_3$) {lit.[7] [α]$^{20}$$_D$: +12.9 (c=1.15, CHCl$_3$)}; 99% ee by chiral HPLC analysis (Chiralcel OD-H column, n-hexane/iPrOH, 97:03, 0.5 mL/min) retention time 17.517 (99.60%) and 15.747 (0.40%) for azido epoxide 5.

Example 7

(2R,3R)-3-Azido-4-phenylbutane-1,2-diol (12)

Optical rotation: [α]$^{20}$$_D$: −30.8 (c=1, CHCl$_3$); 98% ee by chiral HPLC analysis (Chiralcel OD-H column, n-hexane/iPrOH, 90:10, 0.5 mL/min) retention time 13.512 (99.02%) and 13.020 (0.98%).

Example 8

Synthesis of Nosylate (14)

To a solution of azido epoxide 5 (0.2 g, 1.1 mmol) in dry isopropanol (2.0 mL), isobutylamine (0.5 mL, 5.3 mmol) was added, and the reaction mixture was stirred for 5 h at 50° C. It was concentrated under reduced pressure and dried in vaccuo to give 263 mg of amino alcohol 13, which was used for the next step without purification. To a stirred solution of 13 (0.1 g, 0.4 mmol) in dry CH$_2$Cl$_2$ (2.0 mL) was added triethylamine (64 μL, 0.5 mmol) and 4-nitrobenzenesulfonyl chloride (0.11 g, 0.5 mmol) at 0° C. The resulting mixture was stirred for 30 min at this temperature and warmed to room temperature. It was stirred for 12 h and poured into saturated aq. NaHCO$_3$ solution (3 mL) and extracted with Et$_2$O (3×5 mL). The organic layer was dried over anhydrous Na$_2$SO$_4$ and concentrated to give the crude product. Column chromatographic purification using petroleum ether:EtOAc (4:1) provided nosylate 14 (160 mg) as a pure colorless solid (89% over two steps). mp 115-117° C.; [α]$^{20}$$_D$: −5.3 (c=1, CHCl$_3$); IR: (CHCl$_3$, cm$^{-1}$): $\nu_{max}$ 607, 745, 1089, 1160, 1312, 1350, 1531, 2110, 2957, 3499; $^1$H NMR (200 MHz, CDCl$_3$): δ 0.86-0.93 (m, 6H), 1.74-1.91 (m, 1H), 2.76-2.96 (m, 2H), 3.01-3.14 (m, 3H), 3.20-3.23 (m, 1H), 3.57-3.79 (m, 2H), 7.24-7.36 (m, 5H,), 7.98 (d, J=8.9 Hz, 2H), 8.38 (d, J=8.9 Hz, 2H); $^{13}$C NMR (50 MHz, CDCl$_3$): δ 19.7, 20, 26.9, 36.9, 52.2, 58.1, 66.49, 71.4, 124.4, 127.0, 128.5, 128.7, 129.3, 136.8, 144.5, 150.1; Anal. Calcd for C$_{20}$H$_{25}$N$_5$O$_5$S: C, 53.68; H, 5.63; N, 15.65; S, 7.17. Found: C, 53.58; H, 5.54; N, 15.45; S, 7.12%.

Example 9

Synthesis of N-Hydroxyl succinimidyl carbonate of (S)-3-hydroxytetrahydrofuran

To a magnetically stirred solution of (S)-3-hydroxytetrahydrofuran (0.2 g, 2.3 mmol) in 7 mL of dry acetonitrile was added dry triethylamine (0.9 mL, 6.8 mmol) followed by N,N disuccinimidyl carbonate (0.9 g, 3.4 mmol) at room temperature. The mixture was stirred for 4 h and poured into EtOAc (15 mL). The ethyl acetate layer was washed with saturated aq. NaHCO$_3$ solution (5 mL) and dried over anhydrous Na$_2$SO$_4$. The organic extract was concentrated under reduced pressure to give the crude product. Silica gel column chromatographic purification provided the carbonate compound (0.4 g, 82%).

Example 10

Synthesis of 4-Nitro-N-((2R(syn),3S)-2-hydroxy-4-phenyl-3-(((S)-tetrahydrofuran-3-yloxy carbonylamino)-butyl)-N-isobutylbenzenesulfonamide (15)

To a stirred solution of nosylate 14 (0.1 g, 0.2 mmol) in 2 mL of dry THF, triphenyl phosphine (0.06 g, 0.2 mmol) was added as a lump at 25° C. and the reaction mixture was stirred for 30 min. To this, H$_2$O (0.004 g, 0.2 mmol) was added and the stirring continued for 29 h. After completion of reaction, solvent was removed in vaccuo, water was added and extracted with ethyl acetate (3×5 mL). The organic layer was washed with brine, dried over anhydrous Na$_2$SO$_4$, and concentrated to give the crude amine (0.09 g) as a yellow solid which was used in the following step without purification. To a solution of the above crude amine (0.08 g, 0.2 mmol) in 1 mL of dry CH$_2$Cl$_2$ was added N-hydroxyl succinimidyl carbonate of (S)-3-hydroxytetrahydrofuran (0.04 g, 0.2 mmol) (see previous experiment for its preparation) and dry triethylamine (32 µL, 0.2 mmol) at room temperature. The reaction mixture was stirred for 2 h and concentrated to remove solvent. The residue was dissolved in ethyl acetate and washed with 5% saturated aq. NaHCO$_3$ followed by 5% aq. solution of citric acid. The combined organic layers were washed with brine and dried over anhydrous Na$_2$SO$_4$. The mixture was concentrated to give the crude product, which was purified by column chromatography using petroleum ether:EtOAc (7:3) to give carbamate derivative 15 (0.09 g) as a colorless solid (89% over two steps). mp, 161-163° C.; [α]$^{20}_D$: +15.5 (c=0.2, CHCl$_3$); IR: (CHCl$_3$, cm$^{-1}$): ν$_{max}$ 606, 745, 1029, 1088, 1109, 1159, 1312, 1350, 1530, 1605, 1709, 2960, 3388; $^1$H NMR (200 MHz, CDCl$_3$): δ 0.87 (d, J=6.9 Hz, 3H), 0.89 (d, J=6.9 Hz, 3H), 1.83-1.94 (m, 2H), 2.09-2.13 (m, 1H), 2.93-2.96 (m, 4H), 3.13-3.16 (m, 2H), 3.59-3.65 (m, 2H), 3.75-3.83 (m, 5H), 4.88 (br s, 1H), 5.13 (br s, 1H), 7.22-7.32 (m, 5H), 7.95 (d, J=8.8 Hz, 2H), 8.4 (d, J=8.8 Hz, 2H); $^{13}$C NMR (50 MHz, CDCl$_3$): δ 19.6, 19.8, 26.8, 32.5, 35.1, 52.6, 55.1, 57.5, 66.5, 71.9, 72.7, 75.4, 124.0, 126.6, 128.2, 128.4, 129.1, 136.94, 144.5, 149.8, 155.9; Anal. Calcd for C$_{25}$H$_{33}$N$_3$O$_8$S: C, 56.06; H, 6.21; N, 7.85; S, 5.99. Found: C, 56.16; H, 6.18; N, 7.65; S, 5.93%.

Example 11

Synthesis of Amprenavir (1)

To a solution of carbamate nitro derivative 15 (0.05 g, 0.09 mmol) in 2 mL of EtOAc was added SnCl$_2$.2H$_2$O (0.1 g, 0.5 mmol) at 70° C. The reaction mixture was heated for 1 h until starting material disappeared and the solution cooled to room temperature. It was then poured into saturated aq. NaHCO$_3$ solution and extracted with EtOAc. The organic extract was dried over anhydrous Na$_2$SO$_4$ and concentrated under reduced pressure. It was purified over chromatography using petroleum ether:EtOAc (3:2) to give amprenavir 1 (0.04 g, 90%). IR: (CHCl$_3$, cm$^{-1}$): ν$_{max}$ 757, 1090, 1149, 1316, 1504, 1597, 1633, 1705, 2960, 3371; $^1$H NMR (200 MHz, CDCl$_3$): δ 0.86 (d, J=5.7 Hz, 3H), 0.90 (d, J=6.6 Hz, 3H), 1.78-2.21 (m, 3H), 2.75-3.11 (m, 6H), 3.58-4.11 (m, 7H), 4.25 (s, 2H), 5.01 (br s, 1H), 5.07 (br s, 1H), 6.65 (d, J=8.4 Hz, 2H), 7.20-7.28 (m, 5H), 7.51 (d, J=8.4 Hz, 2H); $^{13}$C NMR (50 MHz, CDCl$_3$): δ 19.9, 20.2, 27.3, 32.8, 35.4, 35.7, 53.8, 55.0, 58.6, 66.8, 72.6, 73.2, 75.3, 114.0, 125.9, 126.5, 128.4, 129.5, 137.7, 150.9, 155.9; Anal. Calcd for C$_{25}$H$_{35}$N$_3$O$_6$S: C, 59.39; H, 6.98; N, 8.31; S, 6.34. Found: C, 59.36; H, 6.81; N, 8.25; S, 6.29%.

Example 12

Preparation of 2-(3(S)-Azido-2(R)-hydroxy-4-phenylbutyl)-N-tert-butyldecahydro-(4aS,8aS) isoquinoline-3(S)-carboxomide (16)

Silica gel (Merck grade 60, 230-400 mesh, 6 Å; 0.2 g), was added to a solution of [3S-(3α,4αβ,8αβ)]-N-(tert-butyl) decahydro-3-isoquinolinecarboxamide (0.06 g, 0.3 mmol) and epoxide 5 (0.05 g, 0.3 mmol) in CHCl$_3$ (1 mL) and the resulting suspension was concentrated under reduced pressure. After standing at room temperature for 16 h, the light brown solid obtained was loaded to a column packed with silica gel and eluted with petroleum ether:EtOAc (7:3) to give the azido alcohol 16 (0.09 g, 85%), essentially a single distereomer, as a colorless solid. mp 154.2° C. (lit.$^{12}$ mp 153-5° C.); [α]$^{20}_D$: −75.5 (c=1 CHCl$_3$) {lit.$^7$ [α]$^{20}_D$: −75.7 (c=1, CHCl$_3$)}; IR: (CHCl$_3$, cm$^{-1}$): ν$_{max}$ 1045, 1153, 1226, 1385, 1454, 1519, 1652, 2101, 2861, 2924, 3439; $^1$H NMR (200 MHz, CDCl$_3$): δ 1.33 (s, 9H), 1.25-2.05 (m, 12H), 2.43 (m, 2H), 2.68-3.09 (m, 5H), 3.56-3.64 (m, 3H), 5.84 (s, 1H), 7.23-7.32 (m, 5H); $^{13}$C NMR (50 MHz, CDCl$_3$): δ 20.8, 25.9, 26.1, 28.7, 30.6, 31, 33.3, 36.1, 36.7, 51.1, 58.4, 60.8, 66.9, 70.3, 126.7, 128.6, 129.4, 137.7, 173.3; ESI-MS: m/z 450.5 [M+Na]$^+$ Anal. Calcd for C$_{24}$H$_{37}$N$_5$O$_2$: C, 67.42; H, 8.72; N, 16.38. Found: C, 67.40; H, 8.83; N, 16.35%.

The invention claimed is:

1. A process for an enantioselective synthesis of a syn-azido epoxide of formula (+)-5

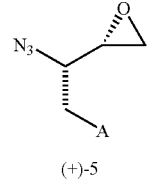

(+)-5 wherein A is an unsubstituted aryl group or substituted aryl group, the substituents being selected from (C1-C8) alkyl, aryl, arylalkyl, halo, and (C1-C8) alkoxy, said process comprising
   i) subjecting an allylic alcohol of formula 7 to epoxidation with m-chloroperbenzoic acid (mCPBA) to obtain a racemic epoxy alcohol;

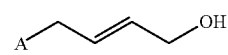

ii) ring opening of the racemic epoxide with azide anion in the presence of a Lewis acid to produce an anti-azido alcohol, followed by selective tosylation of the primary alcohol to afford a tosylate;
   iii) treating the tosylate with a base to obtain a racemic azido epoxide; and
   iv) subjecting the racemic azido epoxide to hydrolytic kinetic resolution to obtain a corresponding 1,2-diol and the syn-azido epoxide, followed by isolating the syn-azido epoxide, said syn-azido epoxide having enantiomeric purity>98%.

2. The process according to claim 1, wherein the Lewis acid is selected from the group consisting of BF$_3$, anhydrous AlCl$_3$, PF$_5$, TiCl$_4$, Ti(OiPr)$_4$, zinc bromide and cerium(III) chloride.

3. The process according to claim 1, wherein the azide anion is supplied from an azide source selected from the group consisting of sodium azide, chlorine azide, bromine azide, iodine azide, tosyl azide, and trimethylsilyl azide.

4. The process according to claim 1, wherein the hydrolytic kinetic resolution comprises the addition of an (S,S)-Co (salen)acetate complex in a concentration in the range of 0.2-0.8 mol %.

5. A process for an enantioselective synthesis of HIV protease inhibitors from a syn-azido epoxide of formula (+)-5

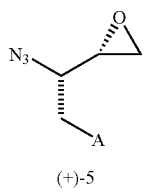

(+)-5 wherein A is an unsubstituted aryl group or substituted aryl group, the substituents being selected from (C1-C8) alkyl, aryl, arylalkyl, halo, and (C1-C8) alkoxy, said process comprising
preparing said syn-azido epoxide by a process comprising:
i) subjecting an allylic alcohol of formula 7 to epoxidation with m-chloroperbenzoic acid (mCPBA) to obtain a racemic epoxy alcohol;

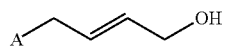

7 ii) ring opening of the racemic epoxide with azide anion in the presence of a Lewis acid to produce an anti-azido alcohol, followed by selective tosylation of the primary alcohol to afford a tosylate;
iii) treating the tosylate with a base to obtain a racemic azido epoxide; and
iv) subjecting the racemic azido epoxide to hydrolytic kinetic resolution to obtain a corresponding 1,2-diol and the syn-azido epoxide, followed by isolating the syn-azido epoxide, said syn-azido epoxide having enantiomeric purity of >98%; and
converting said syn-azido epoxide to said HIV protease inhibitors.

6. The process according to claim 5, wherein the HIV protease inhibitors are selected from Amprenavir, Fosamprenavir, Saquinavir, Darunavir, and Palinavir.

7. The process according to claim 5, wherein the Lewis acid is selected from the group consisting of $BF_3$, anhydrous $AlCl_3$, $PF_5$, $TiCl_4$, $Ti(OiPr)_4$, zinc bromide and cerium(III) chloride.

8. The process according to claim 5, wherein the azide anion is supplied from an azide source selected from the group consisting of sodium azide, chlorine azide, bromine azide, iodine azide, tosyl azide, and trimethylsilyl azide.

9. The process according to claim 5, wherein (S,S)-Co(salen)acetate complex is provided in the hydrolytic kinetic resolution in a concentration in the range of 0.2-0.8 mol %.

10. The process according to claim 5, wherein the HIV protease inhibitor is Amprenavir and the conversion of the syn-azido epoxide into said Amprenavir comprises
(i) subjecting the syn-azido epoxide to a regiospecific ring opening with isobutylamine to give an azido alcohol ii) reacting the azido alcohol with a nosylating agent to obtain an azido nosylate; and
iii) converting the azido nosylate into Amprenavir.

11. The process according to claim 10, wherein the nosylating agent is selected from para-nitrobenzenesulfonyl isocyanate, para-nitrobenzenesulfonyl anhydride, and para-nitrobenzenesulfonyl chloride.

12. The process according to claim 10, wherein converting the azido nosylate into Amprenavir comprises one or more reductions using a reducing agent selected from the group consisting of $SnCl_2$, $LiAlH_4$, and salts of Li, Al, Mg, Al, Fe, Cu, Ag, and Na.

13. The process according to claim 5, wherein the base is selected from the group consisting of alkali metal oxide, alkaline metal oxide, hydroxide, carbonate, bicarbonate, hydride, alkyl amine, aryl amine, heterocyclic amine, amino acid, and mixtures thereof.

14. The process according to claim 3, wherein the azide anion is supplied as a solution in a solvent selected from the group consisting of dichloromethane, tetrahydrofuran, ethyl acetate, acetone, dimethylformamide, acetonitrile, dimethyl sulfoxide, C1-C6 alkyl alcohol, water, acetic acid, hexane, benzene, toluene, chloroform, petroleum ether, 1,4-dioxane, heptane, and mixtures thereof.

15. The process according to claim 5, wherein the HIV protease inhibitor is Saquinavir and the conversion of the syn-azido epoxide into Saquinavir comprises reacting the syn-azido epoxide with [(3S)-(3α,4αβ,8αβ)]-N-(tert-butyl)decahydro-3-isoquinolinecarboxamide in the presence of silica gel in an organic solvent to yield 2-(3(S)-Azido-2(R)-hydroxy-4-phenylbutyl)-N-tert-butyldecahydro-(4aS,8aS)isoquinoline-3(S)-carbaxomide, and converting the 2-(3(S)-Azido-2(R)-hydroxy-4-phenylbutyl)-N-tert-butyldecahydro-(4aS,8aS)isoquinoline-3(S)-carbaxomide into Saquinavir.

16. The process according to claim 4, wherein the (S,S)-Co(salen)acetate complex is added as a solution in a solvent selected from the group consisting of dichloromethane, tetrahydrofuran, ethyl acetate, acetone, dimethylformamide, acetonitrile, dimethyl sulfoxide, C1-C6 alkyl alcohol, water, acetic acid, hexane, benzene, toluene, chloroform, petroleum ether, 1,4-dioxane, heptane, and mixtures thereof.

17. The process according to claim 8, wherein the azide anion is supplied as a solution in a solvent selected from the group consisting of dichloromethane, tetrahydrofuran, ethyl acetate, acetone, dimethylformamide, acetonitrile, dimethyl sulfoxide, C1-C6 alkyl alcohol, water, acetic acid, hexane, benzene, toluene, chloroform, petroleum ether, 1,4-dioxane, heptane, and mixtures thereof.

18. The process according to claim 9, wherein the (S,S)-Co(salen)acetate complex is provided in a solvent selected from the group consisting of dichloromethane, tetrahydrofuran, ethyl acetate, acetone, dimethylformamide, acetonitrile, dimethyl sulfoxide, C1-C6 alkyl alcohol, water, acetic acid, hexane, benzene, toluene, chloroform, petroleum ether, 1,4-dioxane, heptane, and mixtures thereof.

* * * * *